(12) United States Patent
Tsukioka

(10) Patent No.: US 9,050,598 B2
(45) Date of Patent: Jun. 9, 2015

(54) DIRECTIONAL OBJECT DISPENSER

(71) Applicant: MEDICATEC Inc., Yashio-shi, Saitama (JP)

(72) Inventor: Hiroyasu Tsukioka, Soka (JP)

(73) Assignee: MEDICATEC Inc., Yashio-shi (JP)

( * ) Notice: Subject to any disclaimer, the term of this patent is extended or adjusted under 35 U.S.C. 154(b) by 117 days.

(21) Appl. No.: 14/014,798

(22) Filed: Aug. 30, 2013

(65) Prior Publication Data
US 2014/0076920 A1    Mar. 20, 2014

(30) Foreign Application Priority Data
Aug. 31, 2012    (JP) ................... 2012-191706

(51) Int. Cl.
G01N 35/04 (2006.01)
B01L 9/00 (2006.01)
G01N 35/10 (2006.01)

(52) U.S. Cl.
CPC ............... B01L 9/543 (2013.01); G01N 35/04 (2013.01); G01N 2035/103 (2013.01)

(58) Field of Classification Search
CPC ... G01N 35/04; G01N 2035/103; B01L 9/543
USPC ......... 221/163, 164, 167, 182, 197, 239, 254; 422/65
See application file for complete search history.

(56) References Cited

U.S. PATENT DOCUMENTS

| | | | |
|---|---|---|---|
| 2,609,912 A * | 9/1952 | Engel | 198/397.06 |
| 2,649,214 A * | 8/1953 | McGowan et al. | 414/327 |
| 2,891,697 A * | 6/1959 | Beckers | 221/156 |
| 3,447,707 A * | 6/1969 | Furst | 414/414 |
| 4,008,826 A * | 2/1977 | Carree | 221/13 |
| 4,099,609 A * | 7/1978 | Kieronski et al. | 198/395 |
| 4,436,197 A * | 3/1984 | MacDonald | 198/389 |
| 5,062,521 A * | 11/1991 | Hockman | 198/389 |
| 5,899,358 A | 5/1999 | Daumueller | |
| 6,227,407 B1 * | 5/2001 | Simeri et al. | 221/254 |
| 6,371,330 B1 * | 4/2002 | Knez | 221/200 |
| 6,478,185 B2 * | 11/2002 | Kodama et al. | 221/6 |
| 6,799,696 B2 * | 10/2004 | Okada et al. | 221/200 |
| 7,228,955 B2 * | 6/2007 | Comas Corral | 198/527 |
| 7,504,067 B2 * | 3/2009 | Itoh | 422/63 |
| 7,931,861 B2 * | 4/2011 | Kitagawa | 422/63 |

(Continued)

FOREIGN PATENT DOCUMENTS

| | | |
|---|---|---|
| DE | 29609900 U1 | 8/1996 |
| EP | 1295639 A2 | 3/2003 |
| GB | 05668 A | 0/1900 |
| JP | H03-232625 A | 10/1991 |

(Continued)

*Primary Examiner* — Patrick Mackey
(74) *Attorney, Agent, or Firm* — Marvin A. Motsenbocker; MOTS LAW, PLLC

(57) ABSTRACT

A device for dispensing directional objects is comprised of: a case for housing the objects in a horizontal direction; a shutter covering the case and capable of leaving a window; a pivot pivotally supporting the case to allow the case to swing around the pivot; a conveyor including a plurality of slots respectively holding the objects in the horizontal direction and being disposed to receive the objects dropped through the window into the slots; a guide including a bottom end and a slit opened upward to receive the objects dropped from the conveyor and gravitationally feed the objects toward the bottom; and a dropper coupled with the bottom end of the guide, where the objects are dispensed with the tip ends thereof directed downward.

5 Claims, 14 Drawing Sheets

(56) References Cited

U.S. PATENT DOCUMENTS

| | | | |
|---|---|---|---|
| 8,403,010 B2 * | 3/2013 | Taniguchi et al. | 141/171 |
| 2004/0108330 A1 * | 6/2004 | Itoh | 221/289 |
| 2008/0220708 A1 | 9/2008 | Maki | |
| 2012/0171078 A1 * | 7/2012 | Kaneko | 422/65 |
| 2013/0116102 A1 * | 5/2013 | Hansen | 494/10 |

FOREIGN PATENT DOCUMENTS

| | | |
|---|---|---|
| JP | 2000-019182 A | 1/2000 |
| JP | 2002-326716 A | 11/2002 |
| JP | 2003-083999 A | 3/2003 |
| JP | 2011-059012 A | 3/2011 |

* cited by examiner

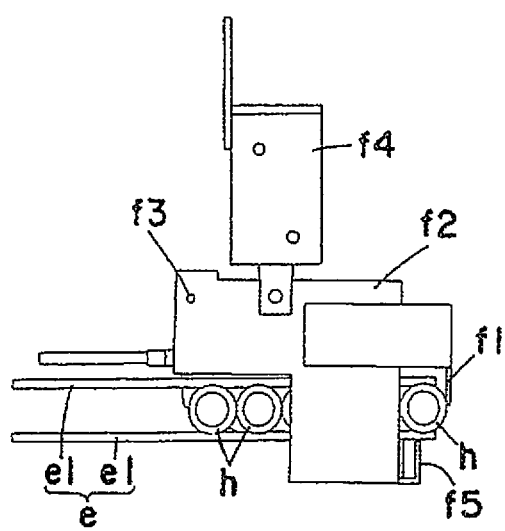
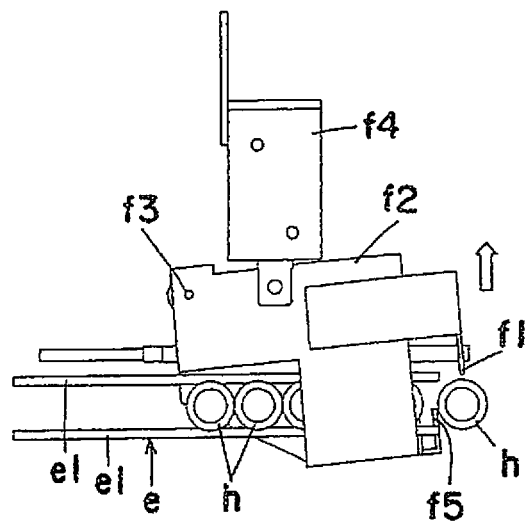

DIRECTIONAL OBJECT DISPENSER

CROSS-REFERENCE TO RELATED APPLICATIONS

This application is based upon and claims the benefit of priority from the prior Japanese Patent Application No. 2012-191706 (filed Aug. 31, 2012); the entire contents of which are incorporated herein by reference.

BACKGROUND OF THE INVENTION

1. Field of the Invention

The present invention relates to a dispenser for dispensing directional objects, such as pipette tips, directed in a particular direction.

2. Description of the Related Art

Before automatically carrying out a biomedical test with respect to a plurality of specimens, a corresponding number of tips should be arranged in multiple lines and multiple rows and then set in a rack. The rack with the arranged tips is subsequently served for the test. Each tip is, however, directional and should be therefore directed in a particular direction in the rack. To direct the tip a particular direction is a very bothersome work if manually done. Thus there have been proposed some devices for automatically carrying out this work.

Japanese Patent Application Laid-open No. 2002-326716 discloses a related art. In the disclosed art, as illustrated in FIGS. 15 through 19 appended to this specification, a number of tips 80 are accommodated in a box-shaped container 1 and reciprocating motion of a lift-up plate 3 pushes out some of the tips 80. Then the pushed-out tips 80 fall down onto a shooter 6 and slip into a slot formed thereon. The tips 80 stand in a row on the shooter 6.

SUMMARY OF THE INVENTION

In the device illustrated in FIGS. 15 through 19, the pushed-out tips 80 often fail to slip into the slot and accordingly scatter around the device. Further the reciprocating motion gets the tips 80 to dance and mutually collide, thereby causing considerable damage and noise. Further improvement is desired.

The present invention has been achieved in view of the aforementioned problem. According to an aspect of the present invention, a device for dispensing directional objects each having a flanged end portion and a body with a tip end is comprised of: a case having a cavity so dimensioned as to house the objects in a horizontal direction and an opening over the cavity to receive the objects into the cavity; a shutter slidably attached to the case to cover the opening, the shutter being slidable a direction perpendicular to the horizontal direction to leave a window in the covered opening to allow the objects to get out of the case; a pivot pivotally supporting the case to allow the case to swing around the pivot from a primary position for receiving the objects to a secondary position for dropping the objects through the window; a conveyor including a plurality of slots respectively so dimensioned as to hold the objects in the horizontal direction, the conveyor being so disposed as to receive the objects dropped from the case into the slots; a guide including a bottom end and a slit opened upward and elongated to the bottom end, the guide being so disposed as to receive the objects dropped from the slots into the slit and so inclined as to gravitationally feed the objects caught in the slit toward the bottom end, the slit being wider than the bodies of the objects but narrower than the flanged end portions whereby each of the objects pivots on the flanged end portion caught on peripheries of the slit to direct the tip end downward; and a dropper coupled with the bottom end of the guide to temporarily catch the objects with the tip ends directed downward and configured to one by one drop the objects with the tip ends directed downward.

BRIEF DESCRIPTION OF THE DRAWINGS

FIG. 13A is a plan view of the dropper in a state where the tips are caught.

FIG. 13B is a plan view of the dropper in a state where one of the tips is being released.

DETAILED DESCRIPTION OF THE PREFERRED EMBODIMENT

Certain embodiments of the present invention will be described hereinafter with reference to the appended drawings. It is noted that the drawings are not scaled and therefore dimensions are not limited to those shown therein.

Figure 4:
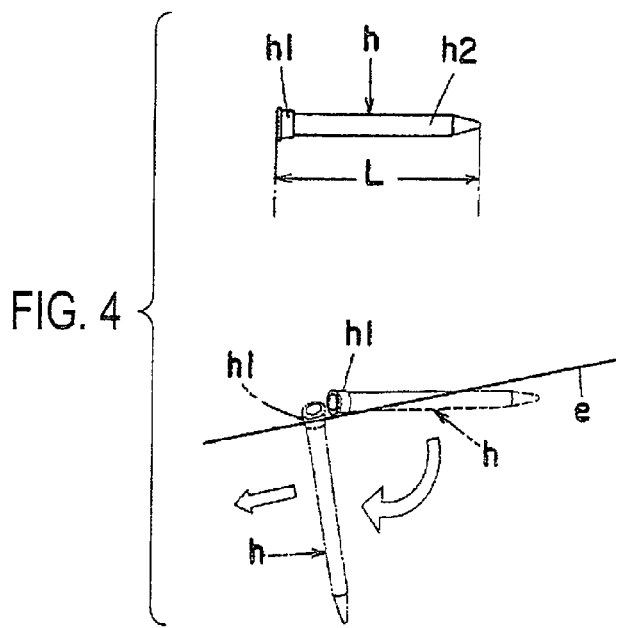
FIG. 4 is a plan view of the tip.

The embodiments may apply to a dispenser which directs directional objects such as pipette tips in a particular direction, particularly where tip ends thereof are commonly directed downward, and then dispenses them into a rack or any container with keeping the direction. A tip h as an object to be dispensed is, as shown in FIG. 4, comprised of a flanged end portion h1 and a body h2 with a tip end.

Figure 1:
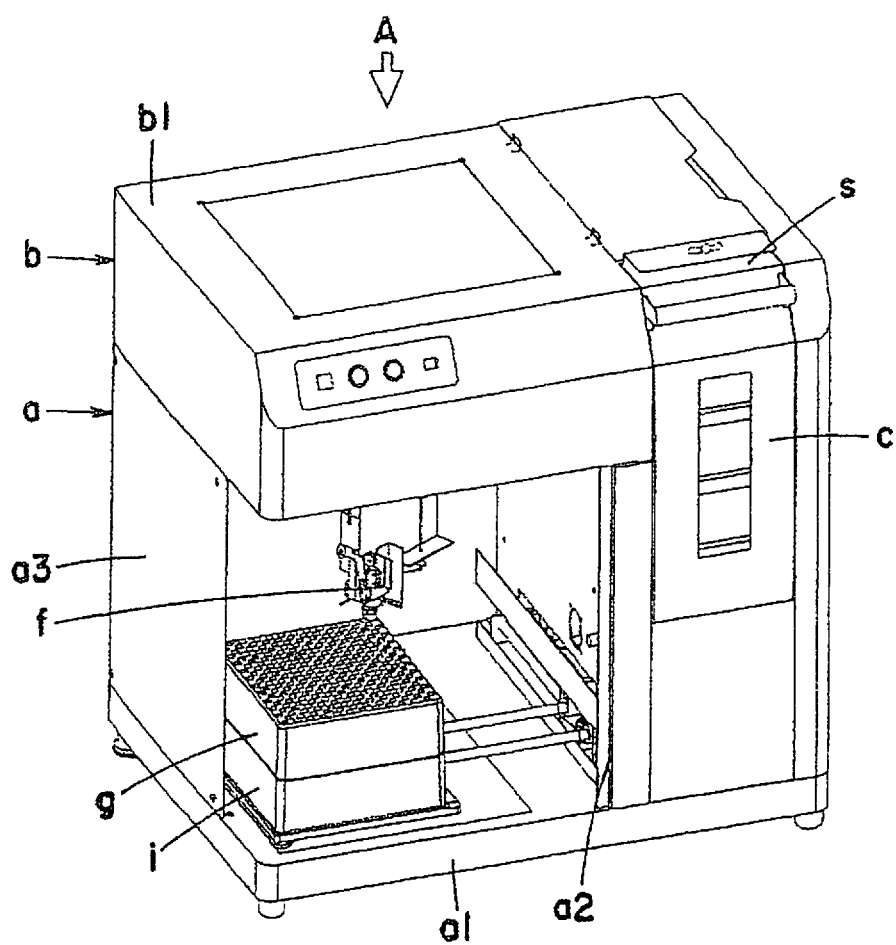
FIG. 1 is a perspective view of a tip dispenser according to an embodiment of the present invention, where a case for housing tips is retracted in a chassis.

Referring to FIG. 1, a tip dispenser A according to an embodiment of the present invention is in general comprised of a chassis a, a controller b, a case c retractable in the chassis a, a conveyor d housed in the chassis a, and a dropper f.

The chassis a is in general constructed of a pedestal a1 and frames a2 standing thereon. Outer walls a3 secured to the frames a2 enclose a cavity but an opening is left at the front thereof. A rack g for receiving tips h is introduced through the opening into the cavity and the dropper f for dropping tips hangs over the rack g in the cavity.

The controller b, which may be housed in the chassis a or in a sub-chassis b1 attached to the chassis a, is to execute electronic control of operatable components such as a conveyor therein.

Figure 2:
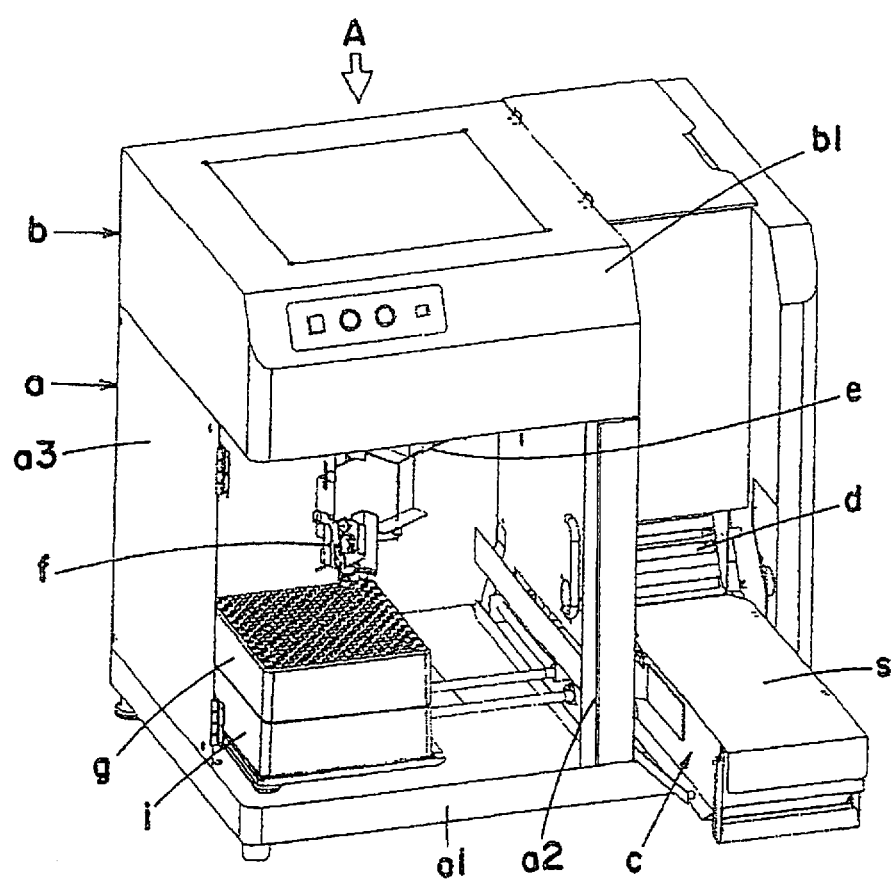
FIG. 2 is a perspective view of the tip dispenser, where the case is pulled down.

The case c is pivoted on the chassis a, thereby being retractable as shown in FIG. 1 and openable as shown in FIG. 2. The case c may, at the opened position shown in FIG. 2, receive the tips h. The case c at the retracted position as shown in FIG. 1 gradually drops the tips h toward the conveyor in the chassis a as described later.

Figure 3:
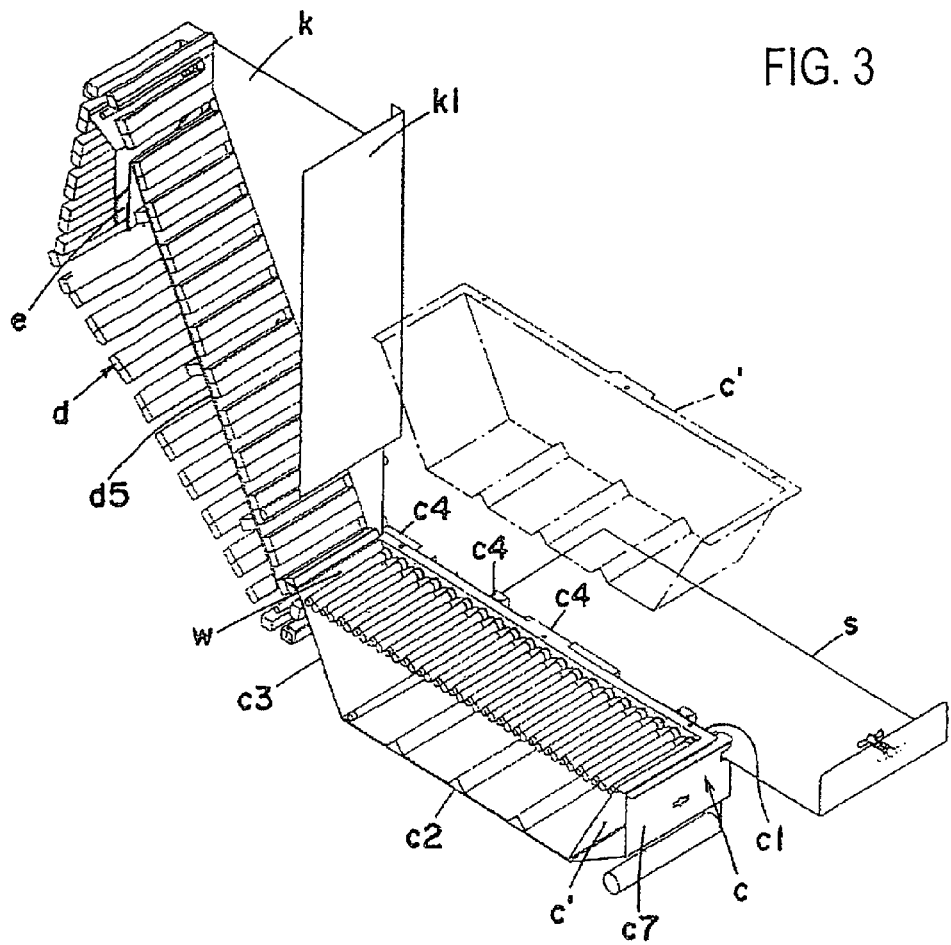
FIG. 3 is a perspective view of a conveyor and the case in the tip dispenser, where the case is pulled down.

Referring to FIG. 3, the case c is generally formed in a boat-like shape and has a cavity defined by paired side walls c1, a bottom wall c2, an end wall c3 and an opposite end wall c7, and an opening opened upward. The width of the cavity of the case c, as defined by the distance between the paired side walls c1, is adapted to a length L of each tip h. More specifically, the cavity is so dimensioned as to house the tips h laid in a horizontal direction, namely in a direction parallel to a lateral direction of the case c from one of the side walls c1 toward the opposite wall c1.

The end wall c3 is parallel to the horizontal direction but oblique to the bottom wall c2. The case c is pivoted around a top of the end wall c3 as described later. Therefore, when the case c is pivotally lifted (retracted in the chassis a), the tips h can roll down along the oblique end wall c3 with keeping the horizontal direction.

Figure 5A:
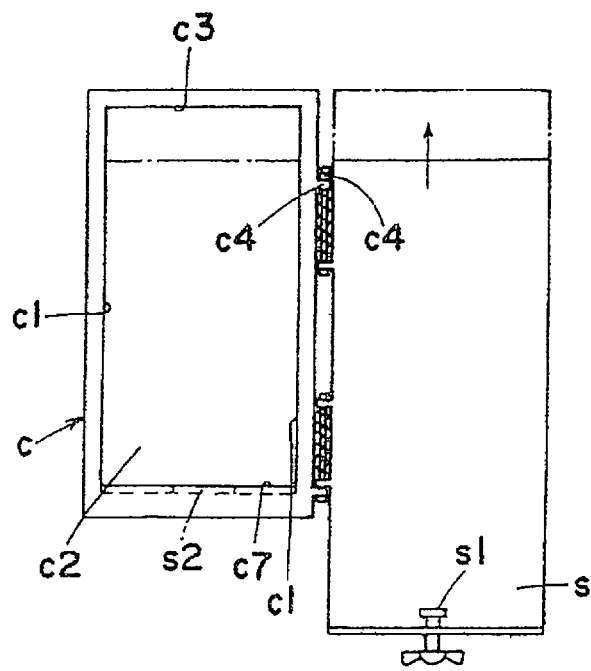
FIG. 5A is a plan view of the case with a shutter.
Figure 5B:
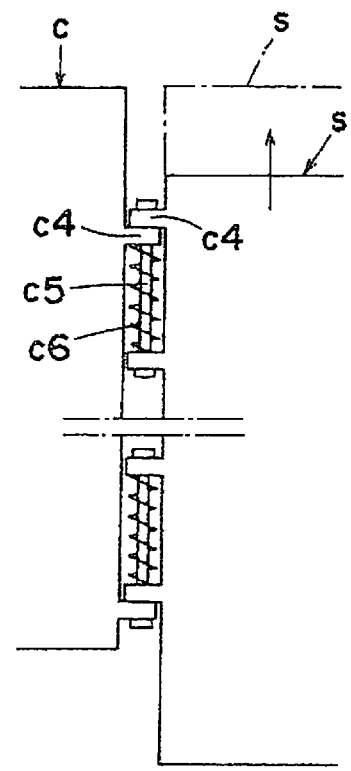
FIG. 5B is an enlarged plan view of the case with the shutter, which mainly shows a joint therebetween.

Referring to FIGS. 5A and 5B in combination with FIG. 3, a shutter s is attached to the case c so as to cover the opening of the case c. Joints between the shutter s and the case c exemplarily applied are hinges c4. The hinges c4 connect the shutter s with the case c side by side so that the shutter s is swingable about shafts c5 inserted in the hinges c4. The hinges c4 is further so structured as to allow slide of the shutter s along the shafts c5 in a direction perpendicular to the horizontal direction. The hinges c4 preferably have springs c6 to urge the shutter s toward a direction opposite to the end wall c3.

More specifically, the shutter s can thoroughly cover the opening if biased against the springs c6, and can leave a window w in the covered opening when it is urged to slide along the shafts c5. As the window w is opened around the end wall c3, the window w allows the tips h to gravitationally get out of the case c when the case c is pivotally lifted.

Figure 6A:
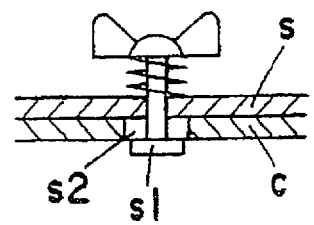
FIG. 6A is a partial elevational sectional view of the case and the shutter, which mainly shows a locking device for locking the shutter with the case.
Figure 6B:
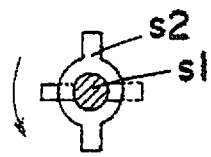
FIG. 6B is a plan view of the locking device.

To temporarily retain the shutter s in a position where the opening of the case c is closed, the shutter s may have a locking device s1 and correspondingly the end wall c7 of the case c may have a keyhole s2 as shown in FIG. 6A. As the locking device s1 is inserted in the keyhole s2 and properly twisted as shown in FIG. 6B, the shutter s is temporarily locked with the case c to close the cavity. When the locking device s1 is disengaged from the keyhole s2, the shutter s is freed and urged by the spring c6 to open the window w.

Figure 7:
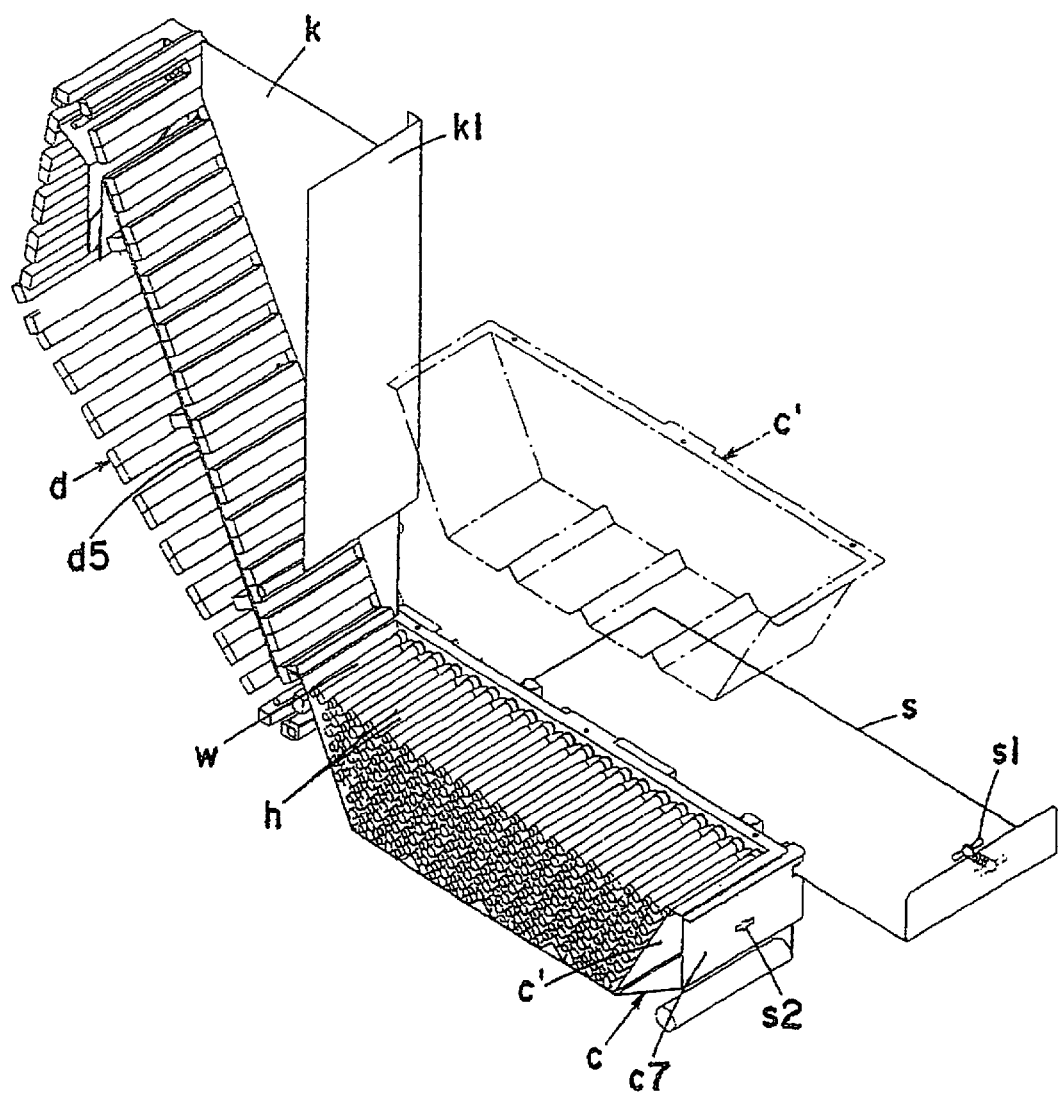
FIG. 7 is a perspective view of the conveyor and the case, in which a sub-case filled with tips is loaded in the case.
Figure 8:
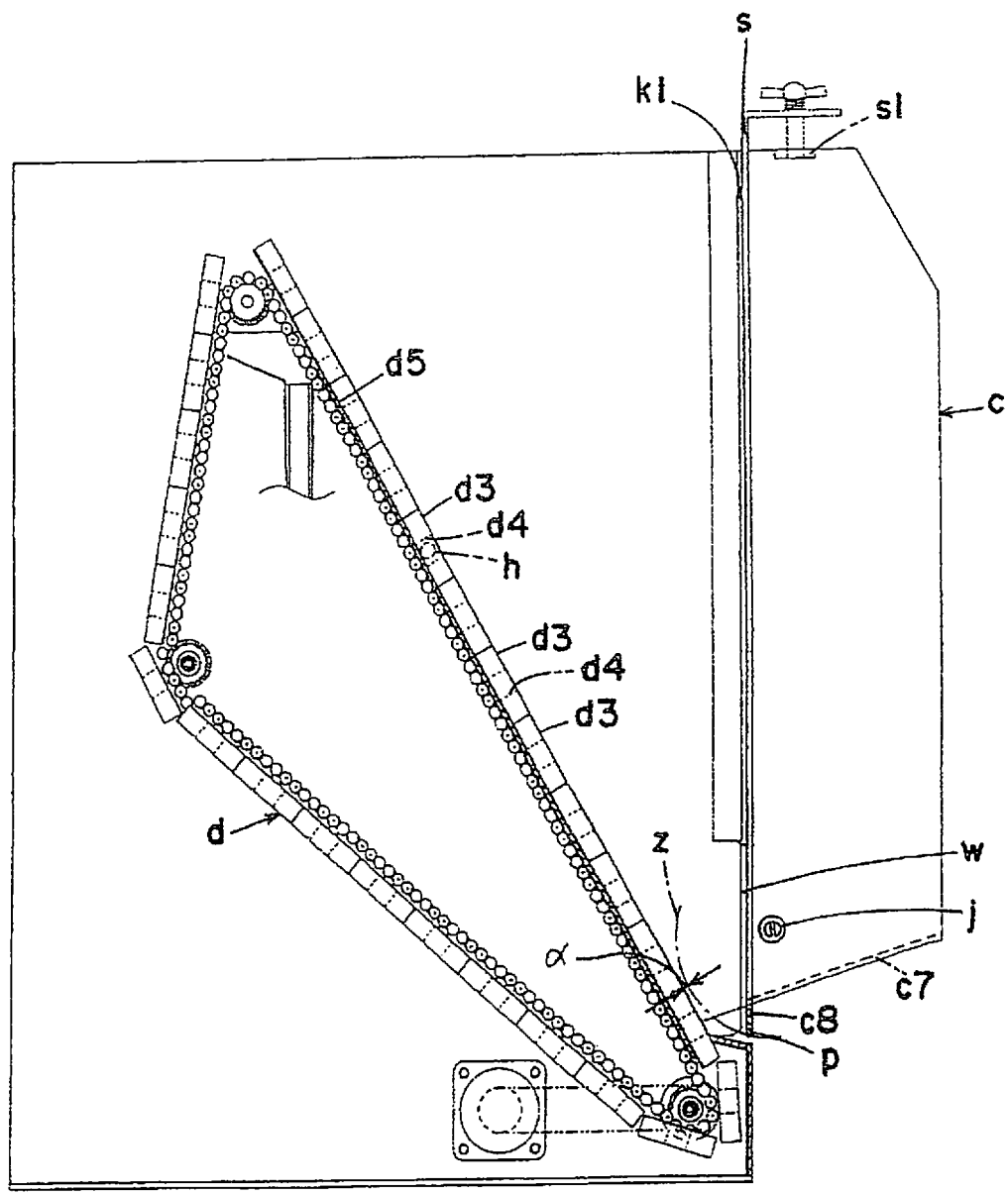
FIG. 8 is an elevational view of the tip dispenser, which shows the interior of thereof.

Referring to FIG. 8, the chassis a is comprised of a pivot j for pivotally supporting the case c. An axis of the pivot j is directed in parallel with the lateral direction of the case c. The case c can thereby swing around the pivot j from an opened position shown in FIGS. 2, 3, 7 and 10 to a retracted position shown in FIGS. 1, 8 and 9. The tips h are loaded in the case c at the opened position and next the case c is swung up around the pivot j and got into the retracted position. The chassis a may have an abutting plate k1 on which the lifted case c rests. Further the chassis a may be further comprised of any locking means for keeping the case c at the retracted position.

Figure 9:
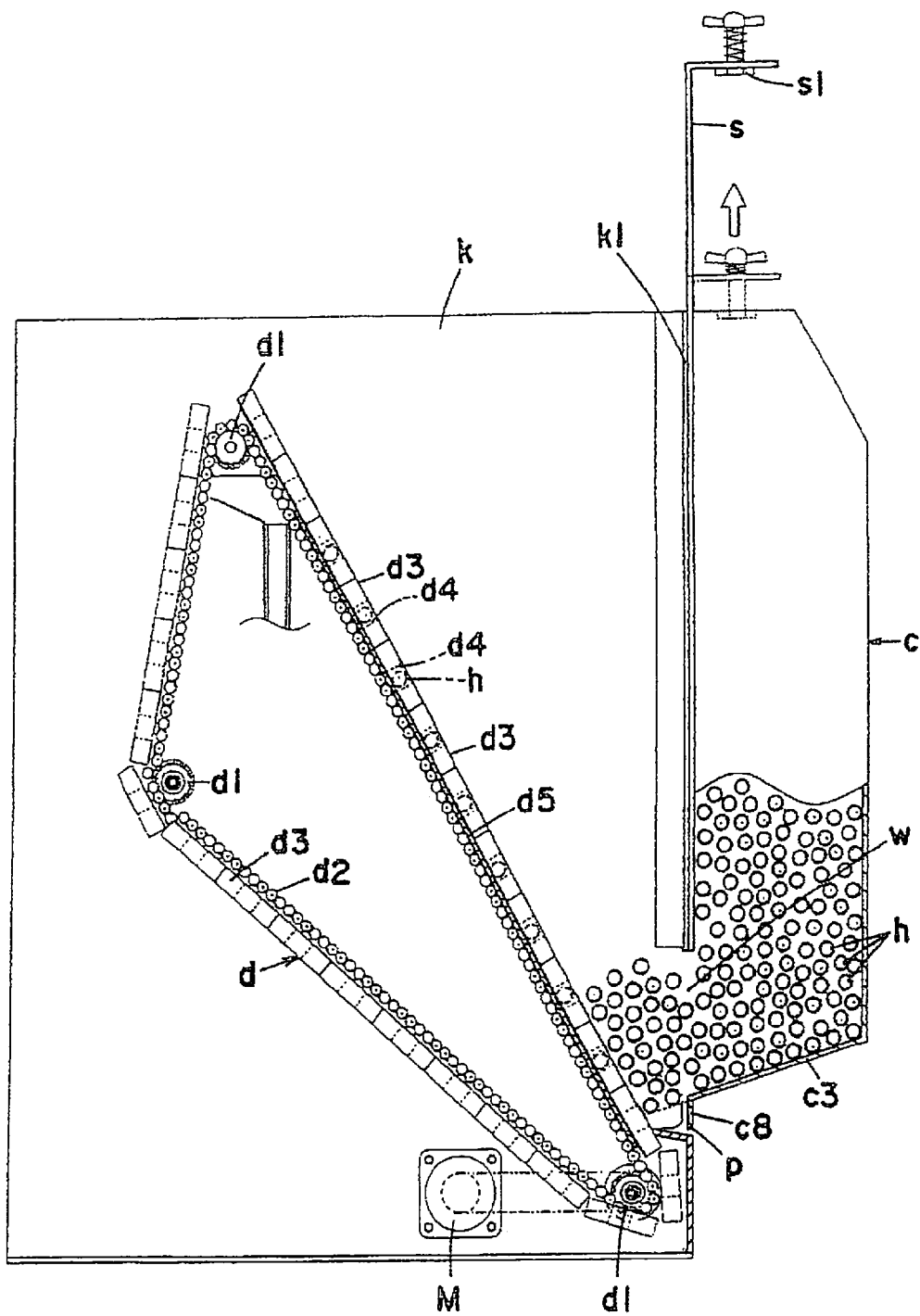
FIG. 9 is an elevational view of the tip dispenser, which shows that the shutter is pulled up to open a window and some tips get out of the case through the window.

The conveyor d is housed in a part k of the chassis a, which is disposed next to the case c. The conveyor d is, not limited to, a belt-like conveyor forming an endless loop powered by a motor M. While the endless loop inherently has an ascending side and a descending side, the ascending side is, around its bottom, made to face the window w of the case c and is properly inclined from the vertical. Due to this arrangement, the conveyor d receives the tips h falling down from the window w as shown in FIG. 9 and lifts these tips h up.

Any means for preventing the tips h from further falling out of the chassis a may be further provided. One of such means is a flange c8 elongated from the end wall c7. The flange c8 may be properly bent relative to the end wall c7 to seal a gap between the case c and the chassis a, which may be held when the case c is retracted.

Alternatively or in addition, a proper disposition of the pivot j can function as such means. While a dashed line z drawn in FIG. 8 depicts a trajectory described by a lowermost extremity p of the case c when the case c swings, the pivot j could be so disposed as to make a gap α held between the conveyor d and the trajectory z to be narrower than the outer diameters of the tips h. The tips h falling from the case c are, throughout movement of the case c, prevented from going down toward the root of the conveyor d and are therefore further prevented from falling out of the chassis a.

Gearing for driving the conveyor d may include sprockets d1 and chain belts d2 turning around the sprockets d1. One of the sprocket d1 is driven by the motor M, thereby endlessly driving the conveyor d.

Figure 11:
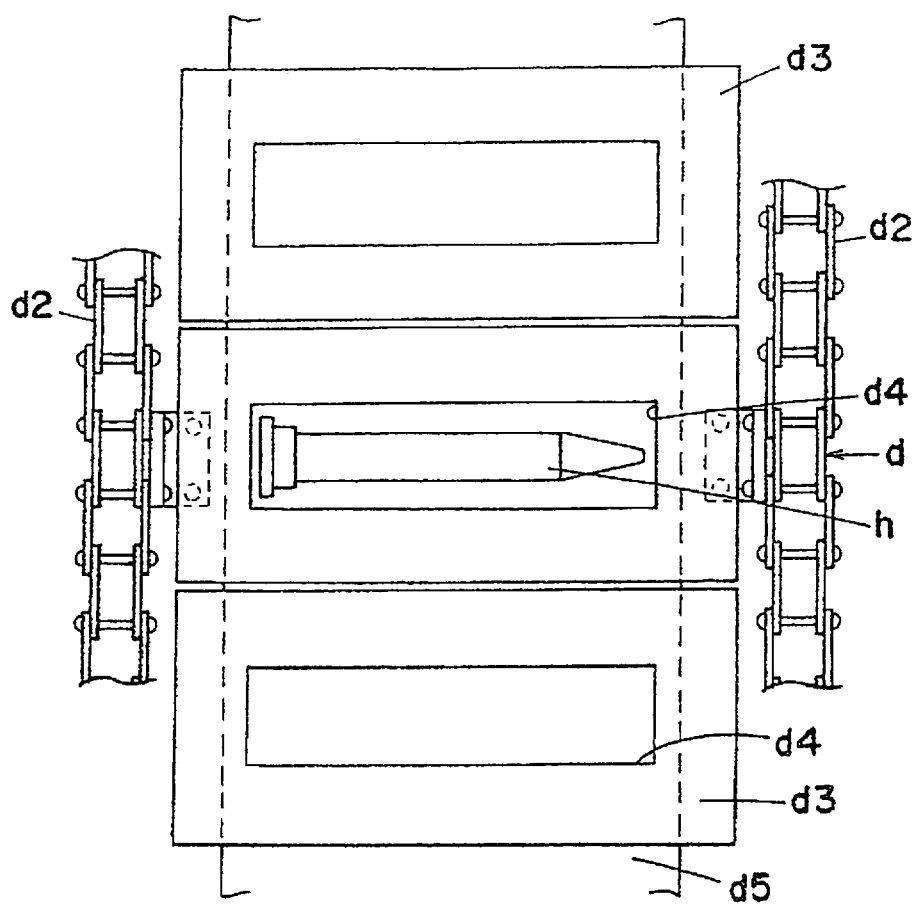
FIG. 11 is an enlarged elevational view of the conveyor, which shows three plates with slots and a tip held in one of the slots.

Referring to FIG. 11, the conveyor d is comprised of a plurality of plates d3 held between the paired chain belts d2 and arranged side by side. Each plate d3 is, but not limited to, rectangular and long sideways and is sufficiently thick relative to the outer diameters of the tips h. Each plate d3 has a slot d4 so dimensioned as to hold one of the tips h laid in a horizontal direction. As each slot d4 is directed in a direction identical to a direction of the tips h dropping from the case c, the tips h naturally get into the slots d4 one by one.

Each slot d4 may be either bottomed or bottomless. If each slot d4 is formed as a bottomless slot, a bottom plate d5 may be provided so as to prevent the tip h in the slot d4 from falling off. Referring again to FIGS. 7 through 10, the bottom plate d5 runs along, and at the back of, the ascending side of the conveyor d. A border at the top of the bottom plate d5 is disposed close to the top of the ascending side and may be bent downward. When a tip h in a slot d4 reaches the top border, the tip h falls out of the slot d4 there.

Figure 12:
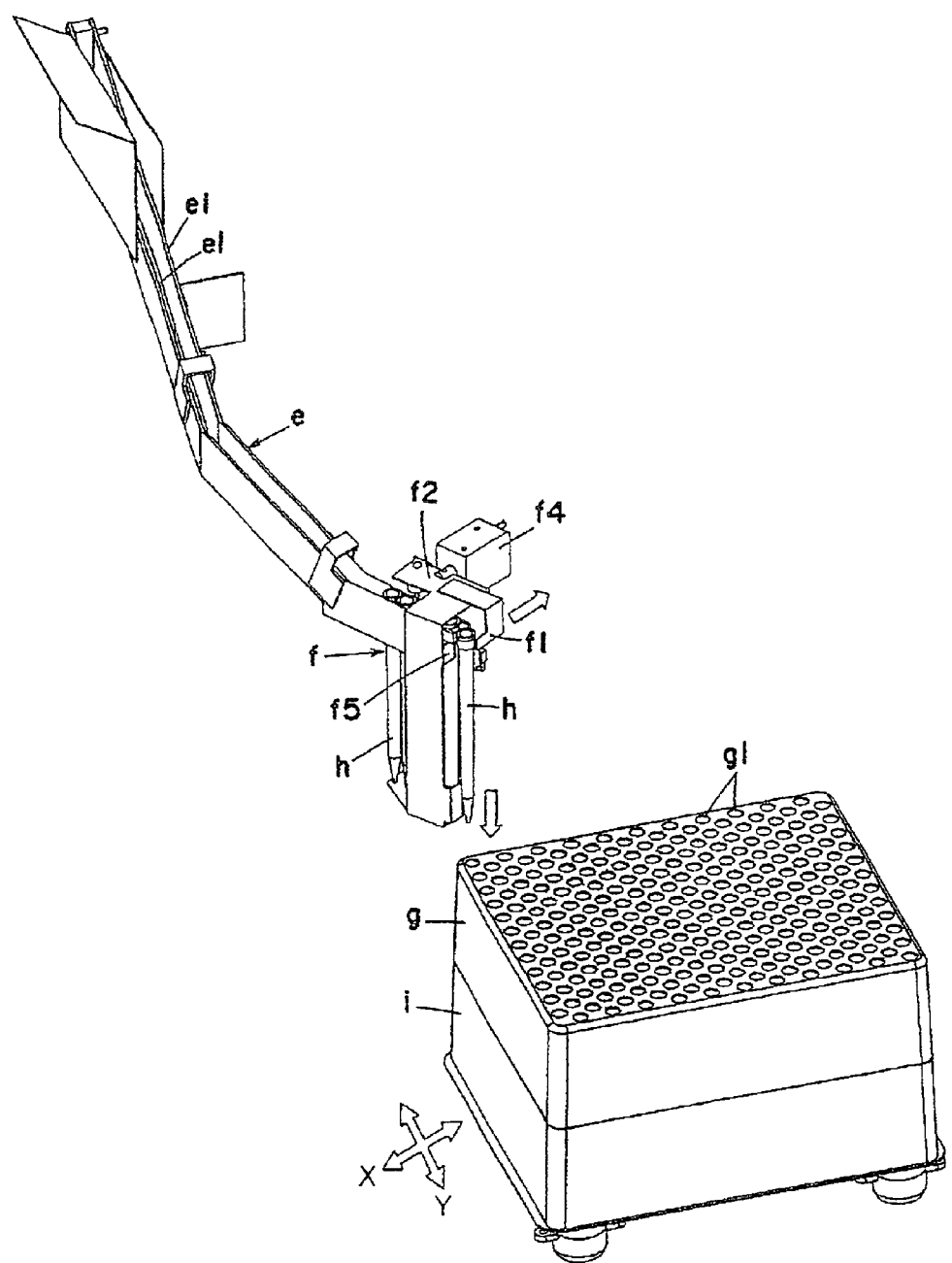
FIG. 12 is a perspective view of a guide, a dropper and a rack, where some tips are fed to the dropper and waiting for being set in the rack.
Figure 14:
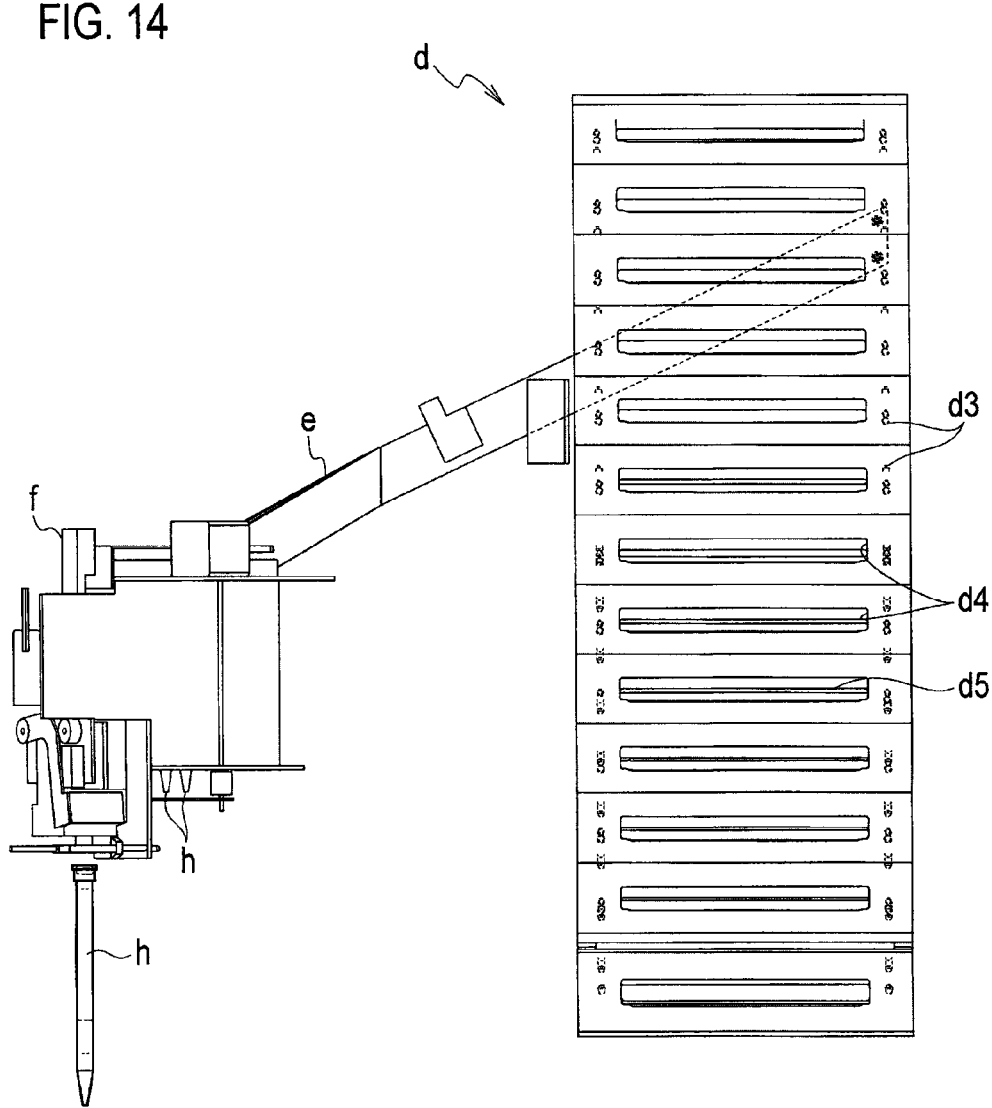
FIG. 14 is an elevational view of the conveyor, the guide and the dropper with one of the tips being dropped therefrom.
Figure 15:
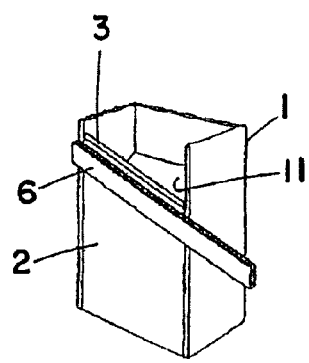
FIG. 15 is a perspective view of a device of the prior art.
Figure 16:
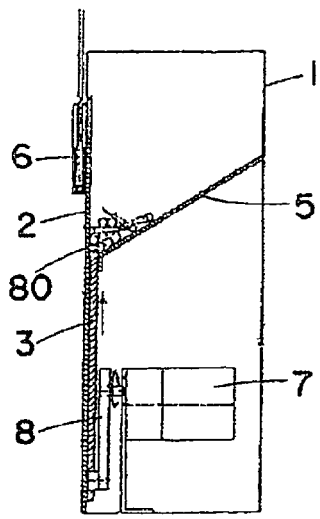
FIG. 16 is a side view of the device of the prior art.
Figure 17A:
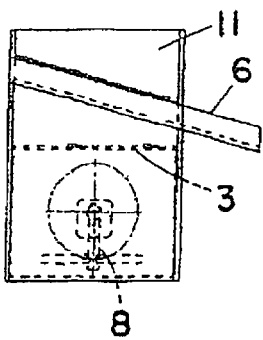
FIGS. 17A through 17C are elevational views of the device of the prior art, which show succeeding steps for dispensing tips.
Figure 17B:
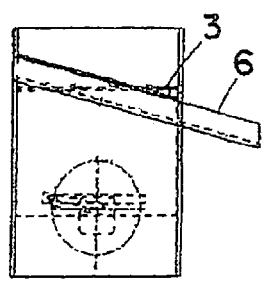
Figure 17C:
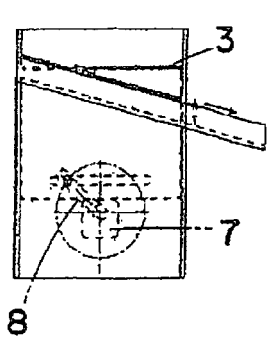
Figure 18:
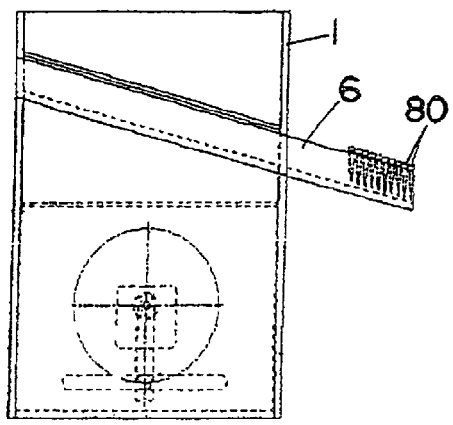
FIG. 18 is an elevational view of the device of the prior art where the tips are arranged in a row.
Figure 19:
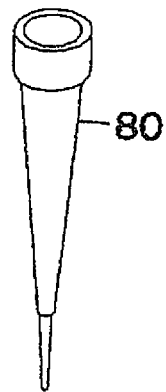
FIG. 19 is a perspective view of a tip used in the device of the prior art.

Below the aforementioned border of the bottom plate d5 provided is a guide e shown in FIGS. 12 and 14. The guide e is formed of paired guide rails e2, which define a slit opened upward. As the slit is disposed just below the border of the bottom plate d5, or the border is directed toward the slit, the guide receive the tips h dropped from the slots d4 into the slit.

The slit defined by the rails e2 is wider than the bodies h2 of the tips h but narrower than the flanged end portions h1. Thus the bodies h1 can get in the slit but the flanged end portions h1 are caught by the rails e2. Referring to FIG. 4, each tip h pivots on the flanged end portion h1 caught by the rails e2, thereby directing its tip end downward.

Referring again to FIGS. 12 and 14, the guide e is inclined so as to gravitationally feed the tips h toward its bottom end.

With the bottom end of the guide e coupled is the dropper f. The dropper f is comprised of a movable frame f2, a stopper f1 and a secondary stopper f5 both secured to the frame f2, and a solenoid f4 for driving the frame f2. The frame f2 is, as pivoted on the pivot f3, swingable between a catching position shown in FIG. 13A and a releasing position shown in FIG. 13B. When the frame f2 is at the catching position shown in FIG. 13A, the stopper f1 crosses over the slit of the guide e and thus catches the tips h fed to the bottom end of the guide e. Then the secondary stopper f5 does not obstruct movement of the tips h. When the frame f2 swings to the releasing position shown in FIG. 13B, the stopper f1 recedes out of the row of the tips h and thus a leading tip h in the row is released. Then the secondary stopper f5 gets into the row so as to catch the succeeding tips h. The frame f2 is operated by the solenoid f4 under the control by the controller b. Therefore the dropper f2 drops the tips h one by one onto the rack g.

The tip dispenser A is further comprised of a movable table i. The table i is made movable both in a direction X and in a direction Y as shown in FIG. 12. To actuate the table i, the tip dispenser A may be comprised of motors and plungers driven by the motors as shown in FIGS. 1 and 2. The table i is driven by the motors via the plungers under the control by the controller b.

The rack g is placed on the table i. The rack g is comprised of a plurality of wells g1. The wells g1 may form a plurality of lines and a plurality of rows.

The tip dispenser A may be operated in the following way.

Figure 10:
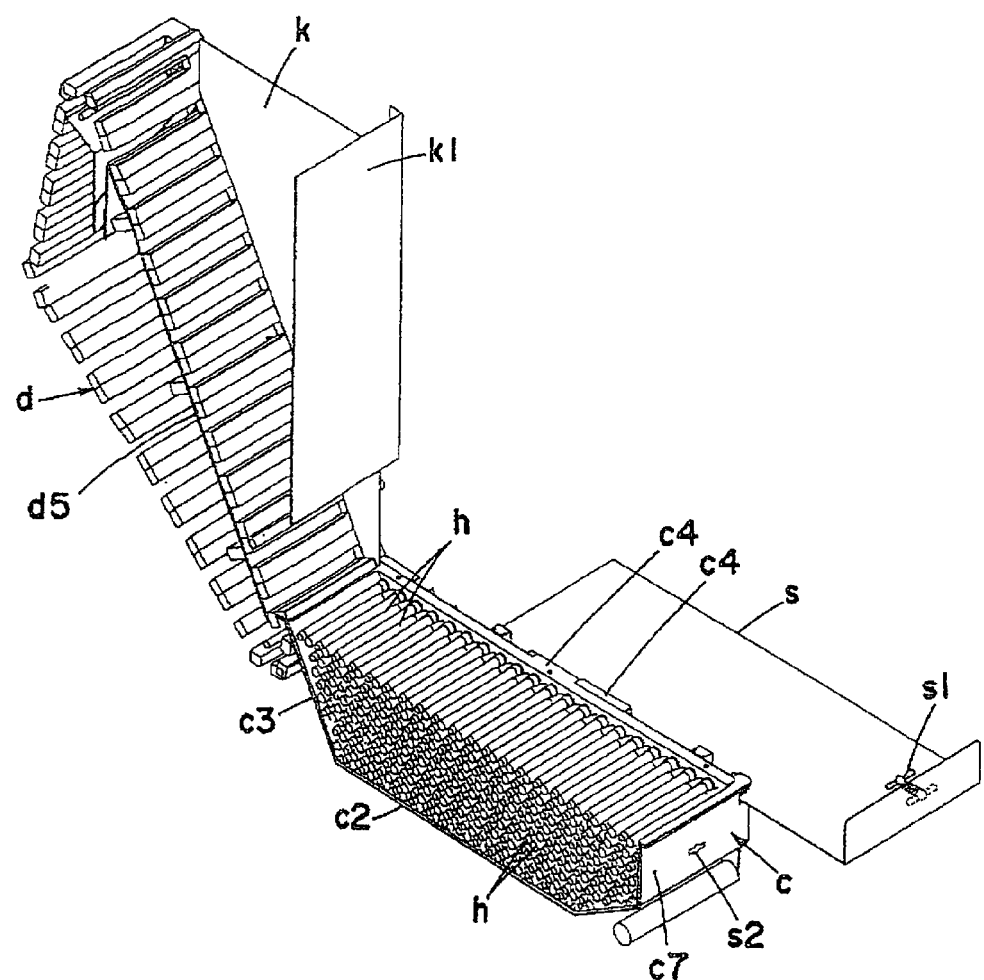
FIG. 10 is a perspective view of the conveyor and the case, in which a number of tips are directly packed in the case.

First a plurality of tips h are loaded into the cavity of the case c. A user may use a sub-case c' as shown in FIGS. 3 and 7, or may directly load the tips h into the case c as shown in FIG. 10. In either case, the tips h are commonly laid in a horizontal direction. The shutter s is made to cover the cavity and is temporarily locked by means of the locking device s1. Then the case c along with the tips h is lifted up and retracted in the chassis s as shown in FIG. 8. Then, as the pivot j is parallel to the direction of the tips h, the horizontal direction as being initially set is retained.

Next the locking device s1 is unlocked and the shutter s is slid upward. Then the window w is opened and some of the tips h still in the case c fall down therethrough. Some of them naturally get into the slots d4. Also in this step the direction of the tips h is retained.

Next the conveyor d is driven to lift the tips h in the respective slots d4. As the precedent tips h move up, following tips h fall down and get into the following slots d4 one after the other.

The lifted tips h fall onto the guide e. The respective tip ends are directed downward thereon and then the tips h are gravitationally fed to the bottom end of the guide e.

The fed tips h are temporarily caught by the dropper f and form a row there. The dropper f is started by the controller b to drop the tips h onto the rack g one by one. As the rack g is driven by the table i under synchronous control by the controller b, the wells g1 are, from end to end, filled with the tips h each having the tip end directed downward.

The present embodiment efficiently prevents objects from falling out because movement of the objects is made within the chassis that is sufficiently sealed. Further the present embodiment enables silent operation and prevents damage to the objects because severe shaking or dancing does not occur during its operation.

Although the invention has been described above by reference to certain embodiments of the invention, the invention is not limited to the embodiments described above. Modifications and variations of the embodiments described above will occur to those skilled in the art, in light of the above teachings.

What is claimed is:

1. A device for dispensing directional objects each having a flanged end portion and a body with a tip end, comprising:
    a case having a cavity so dimensioned as to house the objects in a horizontal direction and an opening over the cavity to receive the objects into the cavity;
    a shutter slidably attached to the case to cover the opening, the shutter being slidable in a direction perpendicular to the horizontal direction to leave a window in the covered opening to allow the objects to get out of the case;
    a pivot pivotally supporting the case to allow the case to swing around the pivot from a primary position for receiving the objects to a secondary position for dropping the objects through the window;
    a conveyor including a plurality of slots respectively so dimensioned as to hold the objects in the horizontal direction, the conveyor being so disposed as to receive the objects dropped from the case into the slots;
    a guide including a bottom end and a slit opened upward and elongated to the bottom end, the guide being so disposed as to receive the objects dropped from the slots into the slit and so inclined as to gravitationally feed the objects caught in the slit toward the bottom end, the slit being wider than the bodies of the objects but narrower than the flanged end portions whereby each of the objects pivots on the flanged end portion caught on peripheries of the slit to direct the tip end downward; and
    a dropper coupled with the bottom end of the guide to temporarily catch the objects with the tip ends directed downward and configured to one by one drop the objects with the tip ends directed downward.

2. The device of claim 1, wherein the case includes an end to be a lowermost extremity of the case when the case is at the secondary position, and the pivot is so positioned as to keep a gap held between the conveyor and a trajectory that the end describes when the case swings from the primary position to the secondary position narrower than outer diameters of the objects.

3. The device of claim 1, wherein the dropper includes a pivoted detent movable from a catching position to a releasing position, a stopper so secured with the frame as to catch a leading object in a row of the objects fed to the bottom end at the catching position and release the leading object at the releasing position, a secondary stopper so secured with the frame as to catch an object next to the leading object at the releasing position and not to obstruct movement of the objects at the catching position, and a solenoid for actuating the frame between the catching position and the releasing position.

4. The device of claim 1, wherein the conveyor forms an endless loop having an ascending side and a descending side, and is so disposed that the ascending side faces the window.

5. The device of claim 4, further comprising:
    a bottom plate running along the ascending side to prevent the objects in the slots from falling and having a border disposed above the guide to allow the objects to falling down to the guide.

* * * * *